United States Patent
Lee

(10) Patent No.: US 11,061,057 B2
(45) Date of Patent: Jul. 13, 2021

(54) NON-CONTACT TYPE MEASURING APPARATUS FOR CONDUCTIVITY AND PERMITTIVITY OF NON-CONDUCTIVE FLUID USING RF SIGNAL

(71) Applicants: MultiPath Co., Ltd., Gyeonggi-do (KR); SEEMS BIONICS INC., Gyeonggi-do (KR)

(72) Inventor: Kyu Young Lee, Seoul (KR)

(73) Assignees: MULTIPATH CO., LTD., Gyeonggi-Do (KR); SEEMS BIONICS INC., Gyeonggi-Do (KR)

( * ) Notice: Subject to any disclaimer, the term of this patent is extended or adjusted under 35 U.S.C. 154(b) by 228 days.

(21) Appl. No.: 16/312,523

(22) PCT Filed: Aug. 10, 2017

(86) PCT No.: PCT/KR2017/008688
§ 371 (c)(1),
(2) Date: Dec. 21, 2018

(87) PCT Pub. No.: WO2018/043947
PCT Pub. Date: Aug. 3, 2018

(65) Prior Publication Data
US 2019/0257868 A1 Aug. 22, 2019

(30) Foreign Application Priority Data
Sep. 1, 2016 (KR) .......... 10-2016-0112407

(51) Int. Cl.
*G01R 27/26* (2006.01)
*G01N 33/26* (2006.01)
*G01N 27/06* (2006.01)

(52) U.S. Cl.
CPC ............ *G01R 27/26* (2013.01); *G01N 27/06* (2013.01); *G01N 33/26* (2013.01)

(58) Field of Classification Search
CPC ................... G01R 27/26; G01N 27/06
(Continued)

(56) References Cited

U.S. PATENT DOCUMENTS

| 4,626,785 A | * | 12/1986 | Hagiwara | ............... G01V 3/28 324/339 |
| 2007/0194792 A1 | * | 8/2007 | Quackenbush | ...... G01N 27/023 324/445 |
| 2016/0016829 A1 | * | 1/2016 | Hughes | ................... C02F 1/487 204/661 |

FOREIGN PATENT DOCUMENTS

| JP | 8-21755 A | 1/1996 |
| JP | 2005-207755 A | 8/2005 |

(Continued)

OTHER PUBLICATIONS

English Translated Chung et al. KR 20110108132 A (Year: 2011).*
International Search Report in corresponding International Appln. No. PCT/KR2017/008688, dated Dec. 5, 2017.

*Primary Examiner* — Melissa J Koval
*Assistant Examiner* — Courtney G McDonnough
(74) *Attorney, Agent, or Firm* — Bacon & Thomas, PLLC

(57) ABSTRACT

Non-contact type measuring apparatus able to detect a difference in signal intensity by transmitting a radio frequency (RF) signal having a predetermined frequency through one of two coil antennas and receiving an induced RF current signal transmitted via a medium through the other coil antennas and detect conductivity and a variation in characteristic of a non-conductor by comparing the signal intensity with a signal intensity comparison table for each frequency, which is stored in a controller by measuring a signal intensity for each frequency in advance, on the basis of the signal intensity for each frequency. The non-contact type measuring apparatus can accurately measure not only various elements using a characteristic in which conductiv- (Continued)

ity is varied according to total dissolved solid, temperature, and an amount of a conductive medium and permittivity change characteristic of a non-conductor, but also conductivity and variation in characteristic of the non-conductor.

9 Claims, 3 Drawing Sheets

(58) Field of Classification Search
USPC ............... 324/324, 325, 353, 453, 439, 698
See application file for complete search history.

(56) References Cited

FOREIGN PATENT DOCUMENTS

| | | | | |
|---|---|---|---|---|
| JP | 2010-515881 | A | 5/2010 | |
| JP | 2012-127752 | A | 7/2012 | |
| KR | 20-0354371 | | 6/2004 | |
| KR | 10-0972563 | B1 | 7/2010 | |
| KR | 20110108132 | * | 5/2011 | ............ G01R 27/26 |
| KR | 10-2011-0108132 | A | 10/2011 | |
| KR | 10-1440444 | B1 | 8/2014 | |
| KR | 10-1512107 | B1 | 4/2015 | |
| KR | 10-1624685 | B1 | 3/2016 | |

\* cited by examiner

NON-CONTACT TYPE MEASURING APPARATUS FOR CONDUCTIVITY AND PERMITTIVITY OF NON-CONDUCTIVE FLUID USING RF SIGNAL

CROSS-REFERENCE TO RELATED APPLICATION

This application is the national stage entry of PCT/KR2017/008688 filed Aug. 10, 2017, which claims priority to and the benefit of Korean Patent Application No. 10-2016-0112407, filed on Sep. 1, 2016, the disclosures of which are incorporated herein by reference in its entirety.

The present invention relates to an apparatus for measuring conductivity of a conductive fluid and a characteristic (permittivity) change of a non-conductive fluid, and more particularly, to a non-contact type measuring apparatus for measuring conductivity of a conductive fluid and permittivity of a non-conductive fluid using a radio frequency (RF) signal without being brought into direct contact with a fluid, which is capable of preventing a problem in that it is difficult for a probe portion in contact with a measurement target to accurately measure the measurement target due to corruption, such as oxidation or contamination and detecting conductivity, turbidity, a temperature change, and a flow rate of a conductive measurement target and a variation in characteristic (permittivity) of a non-conductive measurement target, through measuring of a difference in signal intensity according to a frequency of an RF signal and a difference in signal intensity in the same frequency such that the non-contact type measuring apparatus can be utilized safely, conveniently, and widely in equipment such as water purifiers, washing machines, and boilers, which generally use conductive fluids, and equipment relating to engine oil and various oils, which are non-conductive fluids.

BACKGROUND OF THE INVENTION

Electrical conductivity expresses the extent that a material or solution can transfer charges as a reciprocal of specific resistance. Particularly, a metal has low electrical resistance and excellent conductivity, and an electrolytic solution is affected by concentration of ions, a distance between electrodes, a cross-sectional area of an electrode, a charge size of an ion, and a temperature.

Such measurement of electrical conductivity utilizes a phenomenon in which a change in conductivity occurs due to mixing of foreign materials or the like with a fluid, and measurement of a non-conductive fluid uses a characteristic in which impedance (an alternating current (AC) resistance value) of an antenna for a sensor is varied when permittivity is varied such that a central resonance frequency is changed, utilizing a characteristic in which a non-conductor does not allow electricity to flow but serves as a dielectric substance through which a radio signal passes by charges being accumulated in the non-conductor. As disclosed in the following Patent Documents 1 to 3, measurement of a non-conductive fluid is applied to various fields.

(Patent Document 1) Korean Patent Registration No. 10-1440444

Disclosed are an electrode structure for measuring a bio-signal and an apparatus for measuring an electrocardiogram using the same. The electrode structure includes an electrode plate for acquiring a bio-signal by capacitive coupling with skin of a body, a hygroscopic layer formed on one surface of the electrode plate, and a preamplifier electrically connected to the electrode plate to filter noise of the bio-signal input through the electrode plate and amplify and output the filtered bio-signal. The apparatus for measuring an electrocardiogram includes a first electrode and a second electrode to which the above-described configuration of the electrode structure is applied to measure the bio-signal, a differential instrumentation amplifier in which output signals of the first electrode and the second electrode are input and differentially amplified, a signal processor for receiving an output signal of the differential instrumentation amplifier, filtering noise of the output signal, and amplifying the filtered signal, and a wireless sensor node for performing an analog-to-digital conversion on an output signal of the signal processor and transmitting the converted signal in a wireless manner. According to the above-described configuration, an initial noise stabilization time can be reduced, and a stable electrocardiogram signal can be obtained for a short period of time without noise.

(Patent Document 2) Korean Patent Registration No. 10-1512107

Disclosed are an apparatus and a method for measuring electric conductivity, which are capable of accurately measuring electric conductivity by correcting a measurement error of electric conductivity due to a temperature change of a measurement apparatus, which is caused by a current applied for measuring electric conductivity. The apparatus for measuring electric conductivity includes a sensor part including an input electrode and an output electrode which are provided at a material which will be measured, a signal generator for generating an electrical signal, a signal detector for detecting the electrical signal, N first switches (N>1 and N is an integer) connected in parallel between the signal generator and the signal detector and configured to switch electrical signals from the signal generator to the signal detector, a second switch connected between the signal generator and the input electrode and configured to switch the electrical signal from the signal generator to the input electrode, a switching controller for controlling switching of the N first switches and the second switches, N resistors connected in series to the N first switches, and a signal processor for measuring electrical conductivity of the material using the electrical signals detected by the signal detector according to the switching of the N first switches and the second switches under the control of the switching controller.

(Patent Document 3) Korean Patent Registration No. 10-1624685

Disclosed is an apparatus for measuring an electrocardiogram, wherein the apparatus measures an electrocardiogram signal generated as a heart of a target individual moves. The apparatus includes a first electrocardiogram sensor configured to be in contact with a left hand of the target person, and a second electrocardiogram sensor configured to be separated from the first electrocardiogram sensor by a predetermined distance and to be in contact with a right hand of the target person. At least one of the first electrocardiogram sensor and the second electrocardiogram sensor includes a conductive fiber having predetermined electrical conductivity, and an electrocardiogram signal of the target person is measured when the target person grips the first electrocardiogram sensor and the second electrocardiogram sensor with the two hands. When the first or second electrocardiogram sensor including the conductive fiber is installed and used at a steering wheel of a vehicle, there are effects in that the apparatus has tactility superior to that of a metal terminal, has quick sweat absorption, and is easily harmonized with a material of an outer surface of a general steering wheel.

(Patent Document 4) Korean Utility Model Registration No. 20-0354371

Disclosed are a dielectric soil moisture measuring sensor and a remote real-time data transferring programmed system, which are capable of automatically sensing soil moisture, recording and outputting moisture measurement data, and determining a moisture state of soil more accurately and in real time by configuring a condenser for a soil moisture sensor using soil as a medium and a standard condenser using air as a medium, oscillating high frequency signals through the condenser and the standard condenser, measuring and comparing frequencies or periods of the high frequency signals at the condenser and the standard condenser, converting the measured frequency or period values into corresponding capacitances, and quantifying a water content in the soil. Thus, there is an effect of providing the dielectric soil moisture measuring sensor and a remote real-time data transferring programmed system, which are capable of automatically sensing soil moisture, recording and outputting moisture measurement data, and determining a moisture state of soil more accurately and in real time by configuring a condenser for a soil moisture sensor using soil as a medium and a standard condenser using air as a medium, oscillating high frequency signals through the condenser and the standard condenser, measuring and comparing frequencies or periods of the high frequency signals at the condenser and the standard condenser, converting the measured frequency or period values into corresponding capacitances, and quantifying a water content in the soil.

(Patent Document 5) Korean Patent Registration No. 10-0972563

Disclosed is a determining device for condition of a bridge deck using a dielectric constant, which is capable of efficiently and accurately determining a state of an entire bridge slab surface for a short period of time. Further, disclosed is a determining device for condition of a bridge deck using a dielectric constant, which is capable of accurately determining whether deterioration occurs in a bridge slab regardless of various conditions inside a bridge. Furthermore, disclosed is a determining device for condition of a bridge deck using a dielectric constant, which is capable of determining whether deterioration occurs in a bridge slab regardless of an ambient climate environment.

However, the above-described apparatuses for detecting conductivity have the following problems.

(1) Since a detection portion for detecting conductivity is brought into contact with a target object to detect conductivity, when a detection apparatus is used for a long period of time, there is a risk for the detection portion of being contaminated, damaged, or destroyed.

(2) Owing to such destruction or deformation of the detection portion, a conductivity detection is not accurately performed such that detection accuracy is affected.

(3) Particularly, such a problem is more likely to occur when the detection portion is exposed to a fluid containing a large amount of water moisture, such as in a water supply, a water purifier, or an air conditioner dehumidifier, or a fluid containing sewage or detergent.

(4) Therefore, in the case of an apparatus which directly detects conductivity or detects conductivity and applies the detected conductivity to a total dissolved solid (TDS) or the like, there occurs a problem in that conductivity is not detected or accuracy is degraded even when the conductivity is detected due to abnormality of the detection portion for detecting the conductivity.

(5) Further, a simplified direct contact method cannot transmit appropriate radio frequency (RF) signals for measuring a characteristic of a non-conductor such that a variation in characteristic of the non-conductor cannot be detected. That is, a direct contact portion should have an antenna structure capable of transmitting and receiving an RF signal, but it is difficult to achieve miniaturization and a simplified structure according to a frequency.

SUMMARY OF THE INVENTION

The present invention is directed to a non-contact type measuring apparatus for conductivity and a variation in permittivity of a non-conductive fluid using a radio frequency (RF) signal, which has a structure in which a detection part for sensing conductivity using an RF signal is not brought into direct contact with a fluid such that conductivity is capable of being conveniently and precisely measured by preventing degradation of sensing ability or a function loss of the detection part due to contamination of the detection part by a fluid or due to damage or destruction of the detection part, conductivity and a variation in permittivity of a non-conductive fluid are capable of being safely and accurately measured even in a fluid containing harmful materials such as chemicals, and installation, replacement, and repair are capable of being easily executed.

Particularly, the present invention is directed to a measuring apparatus capable of accurately measuring conductivity and a variation in permittivity characteristic of a non-conductive fluid with a simplified structure, which is configured to detect a difference in intensity of an RF signal by transmitting a reference RF signal through one of two coil antennas and receiving an RF signal transmitted via a medium through the other of the two coil antennas, detect conductivity by comparing the difference in intensity of the RF signal with a RF signal intensity comparison table, which is stored in advance in a controller by measuring a signal intensity in advance according to a type and an amount of a medium on the basis of an intensity of the reference RF signal, determine a degree of turbidity by measuring and comparing a signal intensity at each point by varying a frequency at a predetermined interval within a frequency range accommodated by the transmission and reception coil antennas using a characteristic in which the intensity of the RF signal is varied according to the turbidity, and detect a variation in characteristic of the medium through which the RF signal is transmitted using a characteristic in which, when a non-conductive medium is measured, an object blocking a flow of a current allows the RF signal to pass through as a dielectric capable of accumulating charges and has inherent permittivity so that an impedance value is varied according to a frequency of the RF signal passing through the object such that an intensity of the passing RF signal is varied. Further, the measuring apparatus is capable of safely and conveniently measuring conductivity with a non-contact method by being configured to allow a fluid, from which conductivity and a variation in permittivity characteristic of a non-conductor are measured, to flow through a non-conductive tube inserted into a central portion of each of the two coil antennas.

According to an aspect of the present invention, there is provided a non-contact type measuring apparatus for conductivity and a variation in permittivity characteristic of a non-conductor using an RF signal, the non-contact type measuring apparatus including a non-conductive tube (100) configured to allow a fluid to flow, first and second coil antennas (200a and 200b) configured to be fitted and installed at the non-conductive tube (100) by being spaced a predetermined interval W apart, and a controller (300)

configured to measure and control conductivity and a variation in characteristic of a non-conductor by analyzing a frequency and a signal intensity of an RF signal, wherein the controller (300) transmits the RF signal to a medium in the non-conductive tube (100) through a magnetic field induced by the first coil antenna (200a) to generate an induced current, controls the second coil antenna (200b) to receive an induced current signal having a frequency transmitted through the medium, and detects conductivity of a fluid and a variation in characteristic (permittivity) of a non-conductor by comparing a difference in intensity between the RF signal transmitted from the first coil antenna (200a) and the RF signal received from the second coil antenna (200b) with a difference in intensity of an RF signal varied according to a state of the medium on the basis of a frequency and a signal intensity of the transmitted RF signal, which are stored in advance in the controller (300).

The non-conductive tube (100) may be made of a glass, a ceramic, a synthetic resin, or rubber, and a connector (110) may be provided at both ends of the non-conductive tube (100) so as to connect another tube for supplying a medium.

Each of the first and second coil antennas (200a and 200b) may have a toroidal coil shape and may be formed in a ferrite toroidal type in which an air toroidal or a ferrite core is inserted in a central portion of each of the first and second coil antennas (200a and 200b).

The controller (300) may display at least one of a total dissolved solid (TDS), a temperature, and a flow rate.

Through the detected conductivity, the non-contact type measuring apparatus according to the present invention may inspect water quality through conductivity (a TDS) of a water purifier, detect a rinsing degree of a washing machine or a residual amount of detergent by comparing purity of water flowing into the washing machine and water discharged therefrom, detect a degree of contamination of indoor air by detecting an amount of contaminated material by measuring conductivity of water discharged from an air conditioner and a dehumidifier, detect water quality through conductivity between an inlet and an outlet of tap water, detect an exchange cycle of circulating water in a boiler by detecting a foreign material content in the circulating water through a TDS, detect a coffee concentration of a coffee machine, detect conductivity or a TDS of industrial water, detect a temperature and a flow rate of a fluid, and detect a permittivity change and an exchange cycle of engine oil, which is a non-conductor, according to the hours of use.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF THE INVENTION

Figure 1:
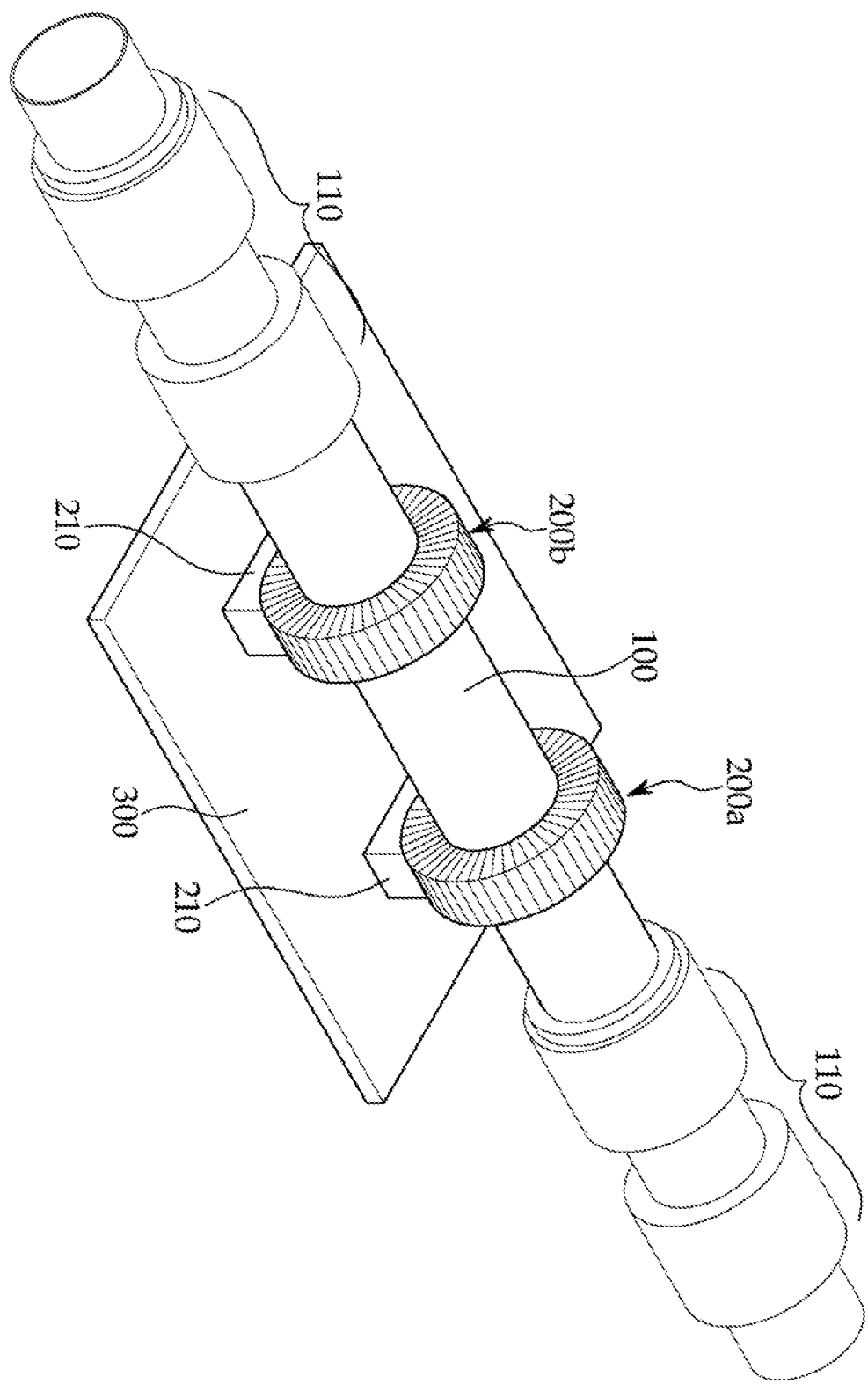
FIG. 1 is a perspective view illustrating an overall configuration of a non-contact type measuring apparatus for conductivity and a variation in characteristic of a non-conductive material according to the present invention.

Hereinafter, exemplary embodiments of the present invention will be described in detail with reference to the accompanying drawings. Prior to description, terms and words used in this disclosure and the appended claims should not be construed as being limited to ordinary or dictionary meanings, and according to the principle that the inventor can appropriately define the concept of the term in order to describe the invention in the best way, the terms and words should be construed as meanings and concepts in accordance with the technical spirit of the present invention.

Therefore, the embodiments described herein and the configurations shown in the drawings are merely the most preferred embodiment of the present invention and do not represent all the technical spirit of the present invention such that it should be understood that there may be various equivalents and modifications capable of substituting the embodiments and the configurations at the time of filing the present application.

(Configuration)

Figure 2:
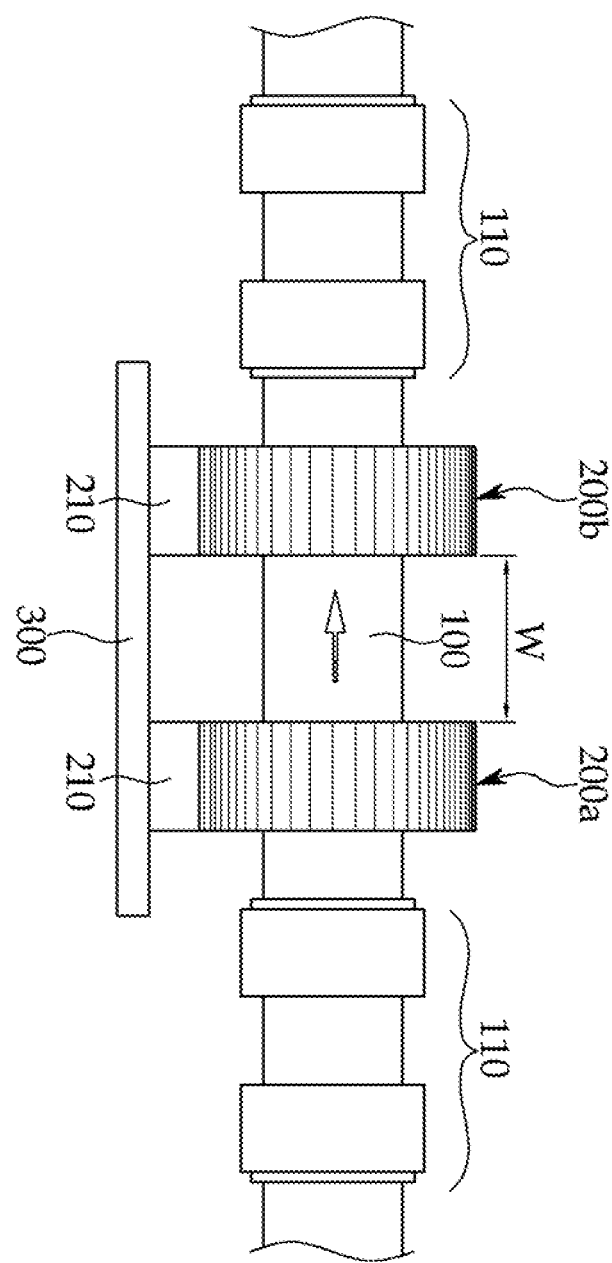
FIG. 2 is a side view illustrating the overall configuration of the non-contact type measuring apparatus for conductivity and a variation in characteristic of a non-conductive material according to the present invention.
Figure 3:
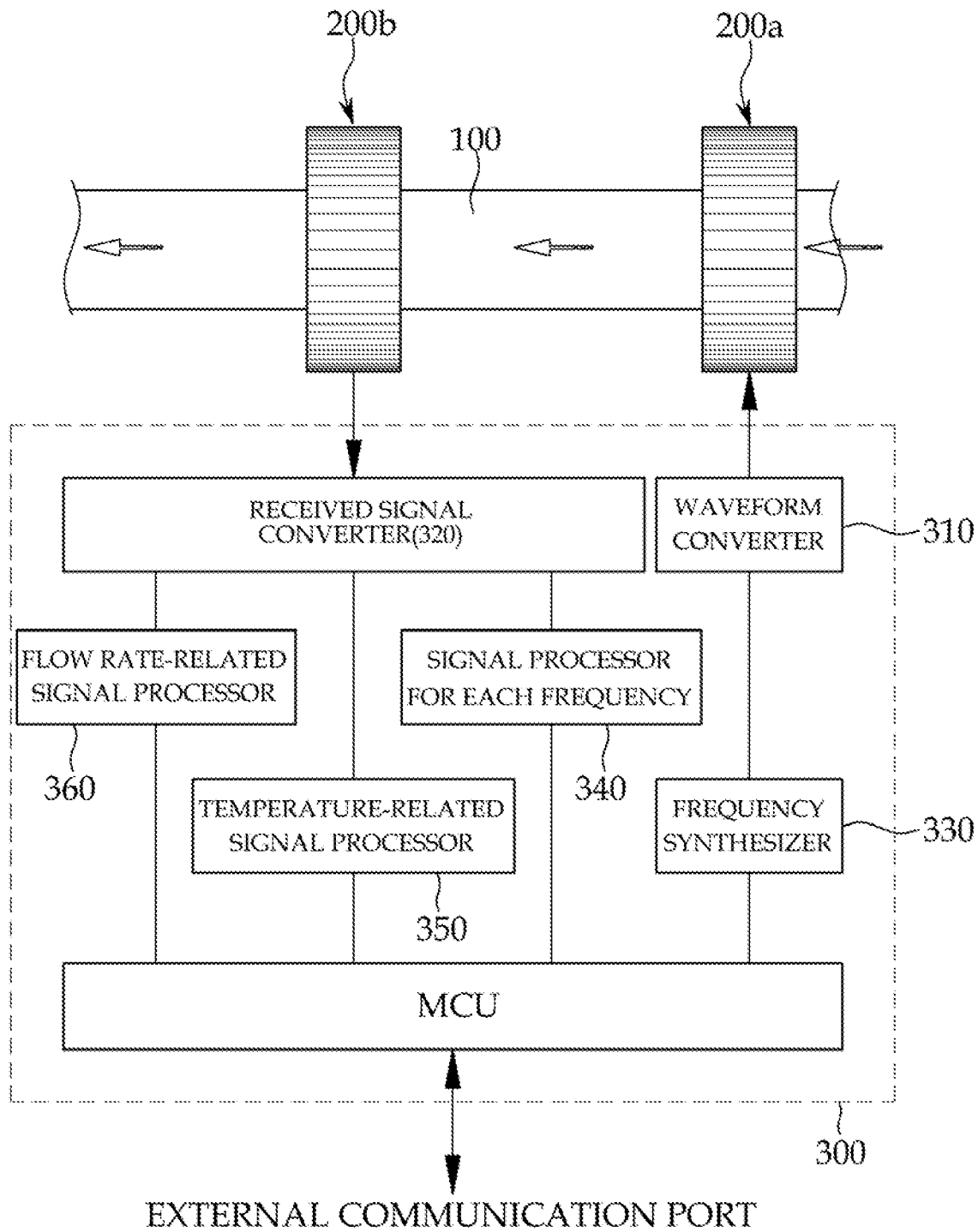
FIG. 3 is a side view illustrating an internal configuration of a controller in the non-contact measuring apparatus for conductivity and a variation in characteristic of a non-conductive material according to the present invention.

As shown in FIGS. 1 to 3, a non-contact type measuring apparatus for conductivity and a variation in permittivity of a non-conductive material using a radio frequency (RF) signal according to the present invention includes a non-conductive tube 100, first and second coil antennas 200a and 200b, and a controller 300.

In this case, the first and second coil antennas 200a and 200b are installed on the non-conductive tube 100 by being spaced a predetermined distance apart, and one of the first and second coil antennas 200a and 200b transmits a radio frequency (RF) signal and the other receives the RF signal. Particularly, the controller 300 compares an intensity difference between the transmitted RF signal and the received RF signal with a signal intensity variation table according to a frequency, which is stored in the controller 300 in advance, thereby measuring conductivity of a fluid with a non-contact method. The controller 300 is capable of analyzing a total dissolved solid (TDS), a temperature, a flow rate, the hours of use by analyzing the measured conductivity, and in the case of a non-conductive medium, the controller 300 is capable of measuring a state variation of a measuring target by analyzing a signal intensity for each frequency passing through the non-conductive medium.

Hereinafter, the above-described configuration will be described in more detail.

As shown in FIGS. 1 to 3, the non-conductive tube 100 refers to a tube through which a fluid flows, wherein conductivity and a variation in characteristic of a non-conductive material will be measured from the fluid. Particularly, since the non-conductive tube 100 should transmit and receive an RF signal through the first and second coil antennas 200a and 200b, which will be described below, the non-conductive tube 100 may be used by being manufactured with a nonconductor so as to not hinder transmission and reception of the RF signal.

In an exemplary embodiment of the present invention, the non-conductive tube 100 may be made of any material as long as it does not hinder the transmission and reception of the RF signal. For example, the non-conductive tube 100 may be made of a glass, a ceramic, a synthetic resin, rubber, or the like.

As shown in FIGS. 1 to 3, in an exemplary embodiment of the present invention, the non-conductive tube 100 may be formed in a straight line shape having a predetermined length and may be configured to allow a fluid to pass through the non-conductive tube 100 in the straight line shape such that a medium passing through the non-conductive tube 100 has linear directivity to increase accuracy of the RF signals, which are transmitted and received. Alternatively, for conductivity measurement only, the non-conductive tube 100 may be formed of a non-conductive tube in the form of a bent shape such as a curved shape.

Lastly, as shown in FIGS. 1 and 2, a connector 110 is provided at both ends of the non-conductive tube 100. The connector 110 refers to a connection hole which is configured to easily connect or disconnect another tube, which is used when a fluid for measurement is supplied to the non-conductive tube 100, to the non-conductive tube 100. The connector 110 may be used by being formed through a conventional technique called as coupling or fitting.

As shown in FIGS. 1 to 3, the first and second coil antennas 200*a* and 200*b* are also called loop antennas and refer to conventional coil antennas, each of which is made by a copper wire being wound in the form of a coil and both ends of the coil are collected into a single circular shape and a magnetic field is induced according to an intensity of a current applied to the coil.

Since an overall shape of the coil antenna is similar to that of a donut, the coil antenna may be easily deformed due to a weak impact applied thereto from the outside. Thus, the coil antenna is manufactured by winding a coil on an iron core, e.g., a ferrite core which is manufactured inside the coil antenna. In this case, the ferrite core, which maintains the overall shape of the coil antenna and has appropriate magnetic permeability so as to easily induce a magnetic field, is used.

In an exemplary embodiment of the present invention, each of the first and second coil antennas 200*a* and 200*b* preferably uses a toroidal coil. This is because the toroidal coil has a magnetic leakage flux less than that of a coil using an "E" type iron core and has less influence on peripheral electronic devices, and particularly, since the magnetic flux leakage is small, accurate measurement is possible. In this case, in consideration of a frequency or a size of an antenna, it is preferable to use a ferrite core having appropriate permeability as the iron core.

In the drawings, an undescribed reference numeral 210 denotes a support for supporting each of the first and second coil antennas 200*a* and 200*b* on the controller 300.

As shown in FIGS. 1 to 3, the controller 300 controls the above-described first and second coil antennas 200*a* and 200*b*, compares intensity differences, which are obtained through the first and second coil antennas 200*a* and 200*b*, of the RF signals varied according to a medium state with a signal intensity reference table, which is previously made and stored, and detects conductivity and a variation in characteristic of a non-conductive material.

FIGS. 1 and 2 illustrate an example in which the controller 300 is formed in a plate shape, i.e., in a substrate shape, and thus those skilled in the art can easily understand that the controller 300 may be formed in any shape as long as it is capable of supporting another configuration.

Meanwhile, as shown in FIGS. 1 to 3, the controller 300 transmits a predetermined RF signal through the first coil antenna 200*a* and receives an RF signal transmitted via a medium in the non-conductive tube 100 through the second coil antenna 200*b*. To this end, as shown in FIG. 3, the controller 300 controls a frequency synthesizer 330 to apply RF signals having various frequencies to the first coil antenna 200*a* and directs signals from the frequency synthesizer 330 to pass through a waveform converter 310 so as to convert the signals into sine waves and suppress unnecessary harmonic signals, thereby supplying the signals passing through the waveform converter 310 to the first coil antenna 200*a*.

Further, as shown in FIGS. 1 to 3, the controller 300 receives an RF signal transmitted via a fluid, which passes through the non-conductive tube 100 in advance, through the second coil antenna 200*b*. At this point, the RF signal picked up through the second coil antenna 200*b* is amplified through a received signal converter 320 and then converted into a direct current (DC) voltage signal to be used in subsequent processing parts according to application. The DC voltage signal converted from the received signal converter 320 is compared with predetermined values, analyzed, and processed in a signal processor 340 for each frequency, a temperature-related signal processor 350, and a flow rate-related signal processor 360 and then is sent to a micro control unit (MCU). Then, the MCU performs an analog-to-digital conversion (ADC) on the DC voltage signal to format the digitally converted DC voltage signal according to a predetermined communication protocol, and the MCU may receive a control signal from the outside and transmit a measured data value using digital communication ports such as RS-232 or a universal serial bus (USB).

Further, the controller 300 detects a difference in intensity by comparing an intensity of the RF signal applied to the first coil antenna 200*a* with an intensity of an RF signal received by the second coil antenna 200*b*. The controller 300 compares the detected difference value with a signal intensity comparison table for each frequency, which is pre-stored in the controller 300, thereby detecting conductivity and a variation in characteristic of the non-conductive material. Here, a "difference with respect to the signal intensity comparison table for each frequency, which is pre-stored in the controller 300" is acquired by obtaining a difference in intensity of an RF signal in advance, which is varied according to a state of a medium on the basis of a frequency applied to the first coil antenna 200*a*, and then storing and using the intensity difference data in the controller 300. A configuration of the signal intensity comparison table is configured by measuring a signal intensity for each of various frequencies being used.

That is, when a fluid flowing through the non-conductive tube 100 is a perfect conductor, a difference in intensity of the RF signal is hardly varied, but in the case of pure water, as an amount of foreign materials in the fluid is increased in the non-conductor, a conductive medium increases and thus conductivity increases such that the difference in intensity of the RF signal becomes larger. Accordingly, in the present invention, an RF signal having a predetermined intensity is applied to purified water, a table representing a difference in intensity of the RF signal according to conductivity is made in advance by varying the conductivity and is stored in the controller 300, a signal having a frequency and an intensity identical to those of the applied RF signal is applied to the first coil antenna 200*a* and then is received by the second coil antenna 200*b* to determine a difference in intensity between the signal and the applied RF signal such that the conductivity may be obtained on the basis of the table stored in the controller 300. Here, since the conductivity increases as an electrolyte concentration is increased in the fluid and the electrolyte concentration is increased as a TDS increases, those skilled in the art can easily understand that the conductivity and the TDS are proportional to each other, and thus when one of the conductivity and the TDS is determined, the other thereof can be easily determined.

Further, since the conductivity is varied within a limited range according to a temperature of a medium, the temperature of the medium may be measured by analyzing such variation. In the case of a medium which maintains a constant temperature and a TDS, a flow rate passing through the medium may be determined through a conductivity value.

Particularly, the non-contact type measuring apparatus for conductivity and a variation in characteristic of a non-conductive material according to the present invention may be easily installed where a fluid is used to detect conductivity and a variation in characteristic of a non-conductive material and may detect a TDS, a temperature, a flow rate, the hours of use, and the like through the detected conductivity. Accordingly, the present invention may be utilized in inspection of a water temperature, a flow rate, the hours of use time, and the like through conductivity (turbidity) of a water purifier, in detection of a rinsing degree of a washing machine or a residual amount of detergent by comparing TDSs of water flowing into the washing machine and water discharged therefrom, in detection of a degree of contamination of indoor air by measuring conductivity of water discharged from an air conditioner and a dehumidifier and measuring an amount of soluble pollutants in the air, in detection of water quality through conductivity between an inlet and an outlet of tap water, in detection of an exchange cycle of circulating water in a boiler according to purity of the circulating water by detecting a foreign material content in the circulating water through a TDS, in detection of a coffee concentration of a coffee machine, in detection of conductivity and a TDS of industrial water, and in detection of a state change (a variation in permittivity) of engine oil and a state change of non-conductive oil (fuel and the like) using a characteristic in which an intensity of an RF signal passing through a non-conductor (dielectric) is varied according to a frequency.

The non-contact type measuring apparatus for conductivity and a variation in permittivity characteristic of a non-conductor using an RF signal according to the present invention has the following effects.

(1) Since a detection part for generating and detecting an RF signal which is used to detect conductivity is not brought into direct contact with a fluid, even though the non-contact type measuring apparatus according to the present invention is used for a long period of time, it is possible to prevent damage or destruction, which may occur when the detection part is exposed to or brought into contact with the fluid, in advance such that durability can be improved.

(2) Particularly, when the detection part is repeatedly exposed to air or liquid for a long period of time for measurement, an oxide film may be formed to act as a factor which hinders an appropriate detection of a signal or degrades detection accuracy by detecting an incorrect signal. However, according to the present invention, since the detection portion performs measurement without being brought into contact with air or a liquid, occurrence of the above-described problems can be prevented in advance.

(3) In the present invention, strength of a magnetic field can be varied through a ferrite core used in a coil antenna, which is used as the detection part, for maintaining the number of turns of a coil and a diameter thereof, concentrating the magnetic field at a central portion of the coil, and maintaining a shape of the coil such that the coil antenna can be manufactured to have an appropriate frequency and an appropriate magnetic field suitable for the purpose of using the measuring apparatus according to the present invention.

(4) Therefore, the measuring apparatus according to the present invention can be conveniently applied to various fields such as a temperature change, a TDS, a flow rate, and as a device for detecting specific ions through the measured conductivity and can be utilized in inspection of water quality through conductivity of a water purifier, in detection of a rinsing degree of a washing machine or a residual amount of detergent by comparing purity of water flowing into the washing machine and water discharged therefrom, in detection of a degree of contamination of indoor air by measuring conductivity of water discharged from an air conditioner and a dehumidifier, in detection of water quality through conductivity between an inlet and an outlet of tap water, in detection of an exchange cycle of circulating water in a boiler according to purity of the circulating water by detecting a foreign material content in the circulating water through a TDS, in detection of a coffee concentration of a coffee machine, in detection of conductivity, a TDS, a temperature, and a flow rate of industrial water, and in measurement of a state change (permittivity) of non-conductive fluid such as engine oil of a vehicle using a characteristic in which an intensity of an RF signal passing through a non-conductor (dielectric) is varied according to an impedance value being varied with change in permittivity value of dielectric.

While the present invention has been described with reference to the embodiments shown in the drawings, these embodiments are merely illustrative and it should be understood that various modifications and equivalent other embodiments can be derived by those skilled in the art on the basis of the embodiments. Therefore, the true technical scope of the present invention should be defined by the appended claims.

What is claimed is:

1. A non-contact type measuring apparatus for conductivity and a variation in permittivity characteristic of a non-conductor using a radio frequency (RF) signal, the non-contact type measuring apparatus comprising:
    a non-conductive tube configured to allow a fluid to flow;
    first and second coil antennas configured to be fitted and installed at the non-conductive tube, wherein the second coil antenna is spaced downstream at a predetermined interval W apart from the first coil antenna; and
    a controller configured to measure and control conductivity and a variation in characteristic of a non-conductor by analyzing a frequency and a signal intensity of an RF signal,
    wherein the controller transmits RF signals having various frequencies to a medium in the non-conductive tube through a magnetic field induced by the first coil antenna to generate an induced current, controls the second coil antenna to receive an induced current signal having the various frequencies transmitted through the medium, and detects conductivity of a fluid and a variation in characteristic (permittivity) of a non-conductor by comparing a difference in intensity between the RF signals transmitted from the first coil antenna and the RF signals received from the second coil antenna with a difference in intensity of an RF signal varied according to a state of the medium on the basis of the frequency and the signal intensity of the transmitted RF signals, which are stored in advance in the controller.

2. The non-contact type measuring apparatus of claim 1, wherein:

the non-conductive tube is made of a glass, a ceramic, a synthetic resin, or rubber: and a connector is provided at both ends of the non-conductive tube so as to connect another tube for supplying a medium.

3. The non-contact type measuring apparatus of claim 1, wherein each of the first and second coil antennas has a toroidal coil shape and is formed in a ferrite toroidal type in which an air toroidal or a ferrite core is inserted in a central portion of each of the first and second coil antennas.

4. The non-contact type measuring apparatus of claim 1, wherein the controller displays at least one of a total dissolved solid (TDS), a temperature, and a flow rate.

5. The non-contact type measuring apparatus of claim 1, wherein, through the detected conductivity, water quality is inspected through conductivity (a TDS) of a water purifier, a rinsing degree of a washing machine, or a residual amount of detergent is detected by comparing purity of water flowing into the washing machine and water discharged therefrom, a degree of contamination of indoor air is detected by detecting an amount of contaminated material by measuring conductivity of water discharged from an air conditioner and a dehumidifier, water quality is detected through conductivity between an inlet and an outlet of tap water, an exchange cycle of circulating water in a boiler is detected by detecting a foreign material content in the circulating water through a TDS, a coffee concentration of a coffee machine is detected, conductivity or a TDS of industrial water is detected, a temperature and a flow rate of a fluid are detected, and a permittivity change and an exchange cycle of engine oil, which is a non-conductor, according to the hours of use are detected.

6. The non-contact type measuring apparatus of claim 2, wherein, through the detected conductivity, water quality is inspected through conductivity (a TDS) of a water purifier, a rinsing degree of a washing machine, or a residual amount of detergent is detected by comparing purity of water flowing into the washing machine and water discharged therefrom, a degree of contamination of indoor air is detected by detecting an amount of contaminated material by measuring conductivity of water discharged from an air conditioner and a dehumidifier, water quality is detected through conductivity between an inlet and an outlet of tap water, an exchange cycle of circulating water in a boiler is detected by detecting a foreign material content in the circulating water through a TDS, a coffee concentration of a coffee machine is detected, conductivity or a TDS of industrial water is detected, a temperature and a flow rate of a fluid are detected, and a permittivity change and an exchange cycle of engine oil, which is a non-conductor, according to the hours of use are detected.

7. The non-contact type measuring apparatus of claim 3, wherein, through the detected conductivity, water quality is inspected through conductivity (a TDS) of a water purifier, a rinsing degree of a washing machine, or a residual amount of detergent is detected by comparing purity of water flowing into the washing machine and water discharged therefrom, a degree of contamination of indoor air is detected by detecting an amount of contaminated material by measuring conductivity of water discharged from an air conditioner and a dehumidifier, water quality is detected through conductivity between an inlet and an outlet of tap water, an exchange cycle of circulating water in a boiler is detected by detecting a foreign material content in the circulating water through a TDS, a coffee concentration of a coffee machine is detected, conductivity or a TDS of industrial water is detected, a temperature and a flow rate of a fluid are detected, and a permittivity change and an exchange cycle of engine oil, which is a non-conductor, according to the hours of use are detected.

8. The non-contact type measuring apparatus of claim 4, wherein, through the detected conductivity, water quality is inspected through conductivity (a TDS) of a water purifier, a rinsing degree of a washing machine, or a residual amount of detergent is detected by comparing purity of water flowing into the washing machine and water discharged therefrom, a degree of contamination of indoor air is detected by detecting an amount of contaminated material by measuring conductivity of water discharged from an air conditioner and a dehumidifier, water quality is detected through conductivity between an inlet and an outlet of tap water, an exchange cycle of circulating water in a boiler is detected by detecting a foreign material content in the circulating water through a TDS, a coffee concentration of a coffee machine is detected, conductivity or a TDS of industrial water is detected, a temperature and a flow rate of a fluid are detected, and a permittivity change and an exchange cycle of engine oil, which is a non-conductor, according to the hours of use are detected.

9. The non-contact type measuring apparatus of claim 1, wherein the controller controls a frequency synthesizer to apply the RF signal having various frequencies to the first coil antenna and directs signals from the frequency synthesizer to pass through a waveform converts to convert the RF signal into sine waves and suppress unnecessary harmonic signals and wherein the RF signal received from the second coil is amplified through a received signal converter and converted into a direct current voltage signal.

* * * * *